United States Patent [19]

Ordahl et al.

[11] Patent Number: 5,266,488
[45] Date of Patent: Nov. 30, 1993

[54] TROPONIN T GENE PROMOTER AND DERIVATIVES THEREOF

[75] Inventors: Charles P. Ordahl; Janet H. Mar; Parker B. Antin; Thomas A. Cooper, all of San Francisco, Calif.

[73] Assignee: The Regents of the University of California, Berkeley, Calif.

[21] Appl. No.: 656,702

[22] Filed: Feb. 19, 1991

Related U.S. Application Data

[63] Continuation of Ser. No. 178,162, Apr. 6, 1988, abandoned.

[51] Int. Cl.$^5$ .................... C12N 15/00; C12N 5/00; C07H 21/00
[52] U.S. Cl. .................... 435/240.2; 536/24.1; 435/317.1; 435/69.1; 435/320.1; 935/22; 935/70; 935/111
[58] Field of Search ............ 536/27; 435/172.3, 240.2, 435/320.1, 317.1, 948; 935/22, 32, 34, 70, 111

[56] References Cited

U.S. PATENT DOCUMENTS 4,650,764 3/1987 Temin et al. .................... 435/240

OTHER PUBLICATIONS

Cooper et al., J. Biol. Chem. 260: 11140–48 (1985).
Bergsma et al., Mol. Cell. Biol. 6: 2462–75 (1986).
Miwa et al., Proc. Natl. Acad. Sci. 84: 6702–6 (1987).
Miller et al., Proc. Natl. Acad. Sci. 80: 4709–13 (1983).
Mar, J. and Ordahl, C., "A Conserved CATTCCT Motif is Required for Skeletal Muscle-Specific Activity of the Cardiac Troponin T Gene Promoter," *Proc. Natl. Acad. Sci. USA* 85, 6404 (1988).
Cooper, T. A. and Ordahl, C. P., "A Single Cardiac Troponin T Gene Generates Embryonic and Adult Isoforms via Developmentally Regulated Alternate Splicing", *J. Biol. Chem.* 260, 11140 (1985).
Miwa, T. and Kedes, L., "Duplicated CArG Box Domains Have Positive and Mutually Dependent Regulatory Roles in Expression of the Human-Cardiac Actin Gene", *Mol. and Cell. Biol.* 7, 2803 (1987).
Salter, D. W. et al., "Transgenic Chickens: Insertion of Retroviral Genes into the Chicken Germ Line," *Virology* 157, 236 (1987).
Salter, D. W. et al., "Gene Insertion into the Chicken Germ Line by Retroviruses," *Poultry Science* 65, 1445 (1986).
Hughes, S. H. and Kosik, E., "Design of Retroviral Vectors for the Insertion of Foreign Deoxyribonucleic Acid Sequences into the Avian Germ Line," *Poultry Science* 65, 1459 (1986).

*Primary Examiner*—Jasemine C. Chambers
*Attorney, Agent, or Firm*—Bell, Seltzer, Park & Gibson

[57] ABSTRACT

The regulatory elements of the troponin T gene promoter are disclosed. These elements comprise, from downstream to upstream, an essential proximal promoter element, a skeletal muscle-specific regulatory element, a cardiac muscle-specific regulatory element, a nonessential positive striated muscle regulatory element, and a nonessential negative regulatory element. Individual ones of these elements may be combined with one another, or with regulatory elements from other promoters, to form additional new promoters with different functional characteristics.

11 Claims, 8 Drawing Sheets

```
cTNT-268
                                                                cTNT-201
CTGGCTGGCTTGTGTCAGCCCCTCGGGCACTCACGTATCTCCGTCCGACGGGTTAAAATAGCAAAAC TCTGAGGCCAC
       |                                                                    |
     -250                                                                  -200 cTNT-129
                                                 |
ACAATAGCTTGGGCTTATATGGGCTCCTGTGGGGAAGGGGGAGCACGGAGGGGGCGGGG CCGCTGCTGCCAAAAT
                        |
                      -150 cTNT-49
                                                           |
AGCAGCTCACAAGTGTTGCATTCCTCTCTGGGCGCCGGGCACATTCCTGCTGTCTGCCCGCCC CGGGGTGGGCGCC
         |                                                              |
       -100                                                            -50

GGGGGGACCTTAAAGCCTCTGCCCCCAAGGAGCCC TTCCAGATAGCCGCGGACCCACCACCGCTCCGTGTGGGAC
                                        |
                                       +1

FIG.2
```

TROPONIN T GENE PROMOTER AND DERIVATIVES THEREOF

This application is a continuation of application Ser. No. 07/178,162, filed 6 Apr. 1988, now abandoned.

BACKGROUND OF THE INVENTION

A promoter is a nucleotide sequence to which RNA polymerase binds so that gene transcription may be initiated. See generally U. Goodenough, *Genetics*, 267-70 (3d ed. 1984). A promoter may consist of a number of different regulatory elements which affect a structural gene operationally associated with the promoter in different ways. For example, a regulatory element might enhance or repress expression of an associated structural gene, subject that gene to developmental regulation, or contribute to the tissue-specific regulation of that gene. Because appropriate modifications to promoters can make possible optimal patterns of gene expression in recombinant DNA procedures, see, e.g., R. Old and S. Primrose, *Principles of Gene Manipulation*, 138-140 (3d ed. 1985), there is a continued need for new promoters having modified functional properties.

A putative cardiac troponin T gene promoter was preliminarily discussed in Cooper, T. A. and Ordahl, C. P., *J. Biol. Chem.* 260, 11140, 11144, 11145 FIG. 6 (1985). This work did not teach the upstream boundary of this promoter, did not disclose the different regulatory elements of which this promoter is comprised, and did not teach how this promoter could be modified (through an understanding of its regulatory elements) to provide new, modified promoters with features different from those of the native promoter. The present invention is based on continued research into the structure of the troponin T gene promoter.

SUMMARY OF THE INVENTION

The present invention is based on the identification of the regulatory elements of the polynucleotide sequence which comprises the troponin T gene promoter. These elements comprise, from that element nearest (most proximal) the native structural gene to that element furthest upstream, (a) an essential proximal promoter element, (b) a skeletal muscle specific regulatory element, (c) a cardiac muscle-specific regulatory element, (d) a nonessential positive striated muscle regulatory element, and (e) a nonessential negative regulatory element. The properties of these elements, and their relation to one another, are explained in detail below. Individual ones of these elements may be combined with one another, or with regulatory elements from other promoters, to form additional new promoters with different functional characteristics.

Figure 1A:
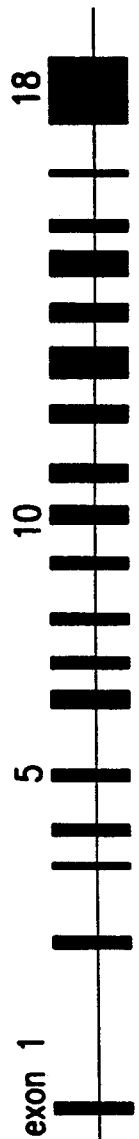
FIG. 1(A, B, C, D) illustrates the construction of expression constructs con he chicken cTNT promoter-/upstream region and the chicken beta-actin promoter region linked to the CAT coding sequence.

(A) The structure of the 9.2 kb chicken cTNT gene. Closed boxes represent the 18 exons of the cTNT gene; thin lines represent intron and flanking sequences.

(B) The cTNT promoter/upstream region. Upper portion is an expanded representation of the 3 kb upstream segment of the cTNT gene shown in (A). T and C represent the putative TATA and CAAT homologies; 5'ut, 5' untranslated region of the cTNT gene; PL, polylinker region; arrow indicates the transcription initiation site. The Ava II site was destroyed in the process of cloning. Lower portion shows the cTNT promoter/upstream deletion segments generated by digestion of the 3 kb segment at the restriction enzymes sites shown. These segments were cloned into pBR-CAT as described in the text.

(C) Structure of pBR-CAT. See Walker, M. D., *Nature* 300, 557 (1983). Solid box, coding sequence of the CAT gene with arrow showing the direction of transcription and the AUG codon is indicated; hatched box, SV-40 splice signal and polyadenylation sequence. Test promoter segments were cloned into the Hind III site. Thin line represents pBR322 sequence; "ori" in open box, origin of replication of pBR322; Amp$^r$, ampicillin resistance gene with arrow showing the direction of transcription.

(D) bACT-275. The beta-actin promoter segment was excised from the beta-actin gene by partial digestion with Hpa II and by complete digestion with Xho I and cloned into pBR-CAT as described in the text. Both the Xho I and Hpa II sites were destroyed in the cloning step. C, T, and PL indicate CAAT and TATA homologies and polylinker region, respectively.

FIG. 2 illustrates the nucleotide sequence of the 5' flanking region of the cTNT gene. The nucleotide sequence of the 5' flanking 268 nucleotides and the first transcribed nucleotides of the cTNT gene was determined as described elsewhere, see Cooper, T. A. and Ordahl, C. P., *J. Biol. Chem.* 260, 11140 (1985). The endpoints of several deletion mutants employed in these studies are shown. The position of a putative CCAAT, SP-1 and TATA homologies are indicated by thin, thick and open bar underlining, respectively. Two copies of a conserved hepatmer, see Nikovits, W. et al., *Nucl. Acids Res.* 14, 3377 (1986), are shown by double underlining. The signature double initiation site for the cTNT gene in embryonic skeletal and cardiac muscle, see Cooper/T. A. and Ordahl, C. P., *J. Biol. Chem.* 2360, 11140 (1985), is shown by the double arrows.

FIG. 3(A, B, C) graphically illustrates the results of tests of the ability of −550/−269 segment to enhance expression from a heterologous promoter.

(A) The cTNT −550/−269 segment was inserted in either a proximal or distal position upstream of the HSV tk promoter in the plasmids pTE−2 S/N or pTE-2, respectively. See Edlund, T. et al. *Science* 230, 912 (1985). Recombinant plasmids with the insert in either a positive or negative orientation relative to its normal position in the cTNT gene were selected and transfected into skeletal muscle and fibroblast cultures.

(B) The average CAT activity and SEM of each parental plasmid and each recombinant is shown. n=number of independent determinations. For details see Methods. Black bars, CAT activity in skeletal muscle cells; stripped bars, CAT activity in chicken embryo fibroblasts.

(C) As in b except that CAT activity was normalized to co-transfected RSV-beta-galactosidase. Values are derived from duplicate samples.

Figures 4A, 4B:
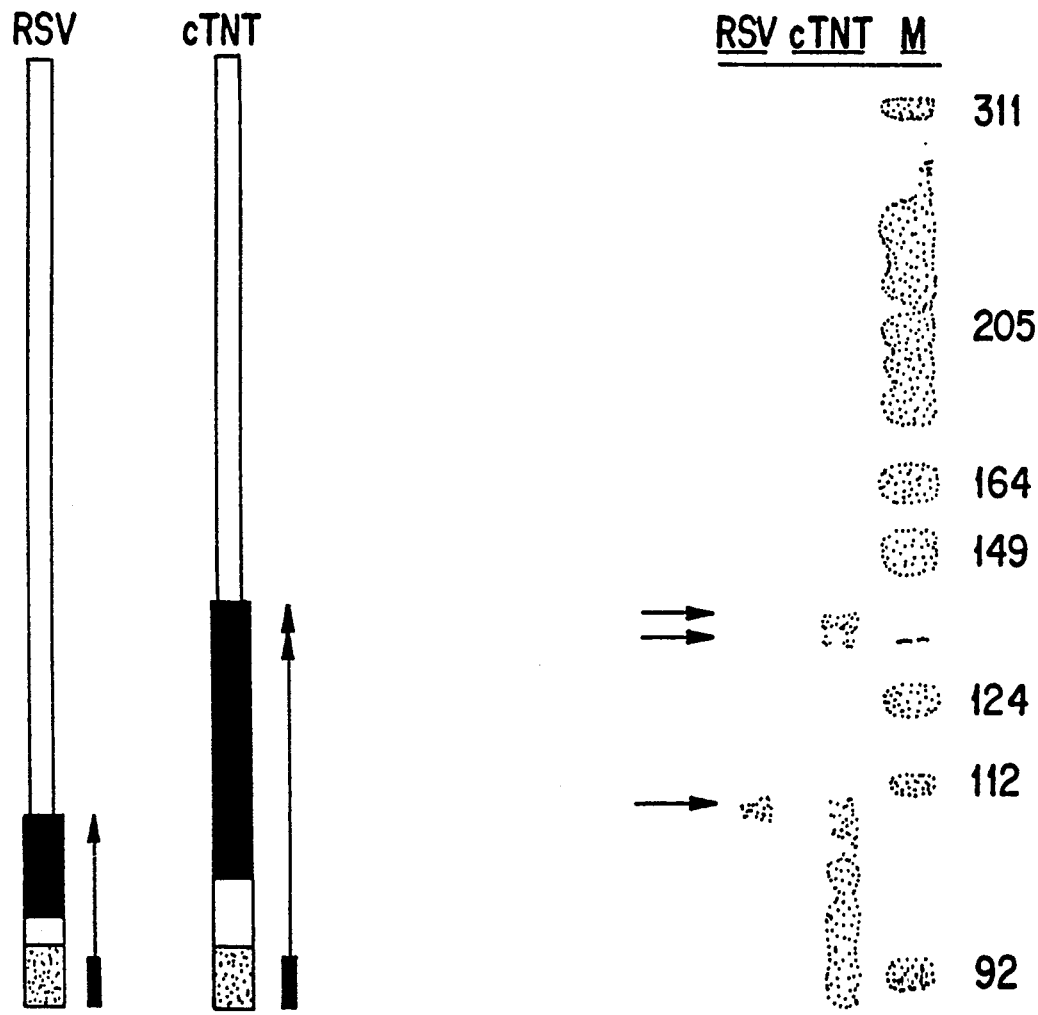

FIG. 4(A,B) shows the primer extension analysis of CAT mRNA in transfected chick primary skeletal muscle cells.

(A) Diagrammatic representation of the structure of the initiation sits regions of RSV-CAT and cTNT-550-CAT. Thin open bar/ 5' flanking DNA; Thick open bar, polylinker DNA; Thick black bar, exon 1 sequence; Thick stippled bar, CAT gene sequence. Thick and thin portions of vertical arrow represent oligonucleotide primer and extended cDNA, respectively. Arrowheads indicate the position of the single expected initiation sits for RSV-CAT and the signature double initiation sites of the cTNT gene.

(B) Autoradiograph of 6% sequence gel showing primer extension run-off products. Horizontal arrowheads show the position of the run-off products for 10 ug total RNA from; (RSV) cultures transfected with RSV-CAT at 109 nucleotides; and (cTNT) the double run-off bands at 145 and 141 nucleotides for cultures transfected with cTNT-550-CAT. Nonspecific terminations below 100 nucleotides were present in both samples but are more visible in the cTNT lane because it was exposed five time longer than the RSV lane. Only the full-length run-off products indicated by the arrows were scanned for quantitation. Size markers are derived from a Hpa II digest of pBR-322 endlabeled with $^{32}$p dCTP using reverse transcriptase.

FIG. 5(A,B) the relative activity of the cTNT promoter segments in embryonic chicken cardiac and skeletal muscle cells.

(A) The CAT activity value for each cTNT promoter segment shown in Table 1 have been normalized to that of cTNT-550 in each cell type. The value of cTNT-49 (see Table 1), which is not active in either cell type, has been subtracted from the CAT activity value of each active cTNT promoter segment. Solid bars, relative CAT activity value in cardiac cells; stippled bars, CAT activity value in skeletal muscle cells.

(B) Diagram of the minimal cTNT promoter segments required for efficient transcription activity. Region which increases the activity of the minimal promoter is shown with +++; thick and thin hatched areas, regions which had a negative effect on cTNT promoter activity in these experiments; arrow indicates transcription initiation site. Solid and stippled blocks indicate minimum regions required for expression in cardiac and skeletal muscle cells, respectively.

DETAILED DESCRIPTION OF THE INVENTION

In the troponin T gene promoter, the essential proximal promoter element contains nonspecific sequences necessary for the initiation of transcription of a structural gene to be operatively associated with the promoter. When +1 designates the first nucleotide of the transcription initiation site, this element is located between nucleotide −49 and nucleotide +1.

The skeletal muscle-specific regulatory element is positioned upstream of the essential proximal promoter element and is operationally associated therewith. This element is necessary for the expression of a structural gene to be operatively associated with the promoter in skeletal muscle cells. The skeletal muscle-specific regulatory element is located between nucleotide −129 and −49.

The cardiac muscle-specific regulatory element is positioned upstream of both the skeletal muscle specific regulatory element and the essential proximal promoter element and is operatively associated with the essential proximal promoter element. This element is necessary for the expression of a structural gene to be operatively associated with the promoter in cardiac muscle cells. The cardiac muscle-specific regulatory element is located between nucleotide −268 and nucleotide −201.

The nonessential positive striated muscle regulatory element is positioned upstream of, and operationally associated with, both the skeletal muscle specific regulatory element and the cardiac muscle-specific regulatory element. This element facilitates the expression of a structural gene to be operatively associated with the promoter in striated muscle cells, both cardiac and skeletal. This element is located between nucleotide −550 and −269.

The nonessential negative regulatory element is positioned upstream of the positive striated muscle regulatory element and is operatively associated therewith. This element inhibits the positive striated muscle regulatory element from facilitating the expression of a structural gene to be operatively associated with the promoter. This element is located between nucleotide −3000 and nucleotide −1100. More broadly defined, this element is located between nucleotide −3000 and nucleotide −550.

A complete promoter (one containing all the elements described above) expresses a structural gene operatively associated therewith in both skeletal and striated muscle cells. The individual elements which comprise a complete promoter can be used in any desired operable combination to produce new promoters having different properties. For example, the negative nonspecific regulatory element can be deleted from a complete promoter so that the expression of a gene associated with the promoter is facilitated. The cardiac muscle-specific regulatory element can be deleted from a complete promoter so that a structural gene operatively associated with the promoter is preferentially expressed in skeletal cells, or the skeletal muscle-specific regulatory element can be deleted from a complete promoter so that a structural gene operatively associated with the promoter is preferentially expressed in cardiac cells. The term "deleted," as used herein, means any modification to a promoter element which renders that element inoperable.

Operable promoters can be constructed from the minimum necessary regulatory elements. One such promoter comprises an essential proximal promoter element and a cardiac muscle-specific regulatory element positioned upstream of the essential proximal promoter element and operatively associated therewith. Another such promoter comprises an essential proximal promoter element and a skeletal muscle-specific regulatory element positioned upstream of said essential proximal promoter element and operatively associated therewith. To these promoters, a positive striated muscle regulatory element may optionally be positioned upstream oft and operatively associated with, the specific regulatory element (skeletal or cardiac).

Further aspects of the present invention are recombinant gene transfer vectors, transformed host cells, and transgenic animals. Recombinant gene transfer vectors of the present invention have a structural gene (e.g., a heterologous gene) and a promoter as described above positioned upstream of the structural gene and operatively associated therewith. The vector may be any construct which is able to replicate with a host cell, including plasmids, viruses, retroviruses, and naked nucleotide sequences. Transformed host cells of the present invention contain a gene transfer vector as described above, in which the promoter is operable in the host cell and the structural gene includes a region coding for a ribosomal binding site operable in the host cell. Suitable host cells may be from animals of different species, including amphibians, reptiles, birds, and mammals, and may be from different animal tissues, including skeletal muscle and cardiac muscle tissue.

Transgenic animals of the present invention comprise a multiplicity of transformed cells containing a gene transfer vector as described above. The promoter is selected to be operable in the transformed cells, and the structural gene includes a region coding for a ribosomal binding site operable in the transformed cells. The tissue of the animal in which the structural gene of the gene transfer vector is expressed depends upon the promoter used in the vector. If the promoter includes both a cardiac muscle-specific regulatory element and a skeletal muscle-specific regulatory element, the structural gene will be expressed in the striated muscle tissue, both skeletal and cardiac, of the animal. If the promoter includes only a cardiac muscle-specific regulatory element, then the structural gene will be preferentially expressed in the cardiac muscle tissue of the animal. If the promoter includes only a skeletal muscle-specific regulatory element, then the structural gene will be preferentially expressed in the skeletal muscle tissue of the animal. Animals of different species may be transformed, including, for example, amphibians, reptiles, birds, and mammals.

One specific method of producing transgenic animals of the present invention is by infecting the animal (e.g., embryo, juvenile, adult) with a gene transfer vector which comprises a retrovirus. One such retroviral vector is the avian leukosis virus. See Salter, D. et al., *Virology* 157, 236 (1987); Salter, D. et al., *Poultry Science* 65, 1445 (1986); Salter, D. et al., *Poultry Science* 65, 1459 (1986). Another is the spleen necrosis virus. See U.S. Pat. No. 4,650,764 to Temin et al. (The disclosures of all references cited herein are incorporated by reference herein as if fully set forth.) Alternatively, transgenic animals may be produced by microinjecting gene transfer vectors of the present invention into animal oocytes, eggs, and embryos. See generally R. Old and S. Primrose, *Principles of Gene Manipulation*, 225-271 (3d ed. 1985).

EXPERIMENTAL

I. MATERIALS

Restriction endonucleases and S1 nuclease were purchased through New England Biolabs, Beverly, Mass. or Boehringer-Mannheim, Indianapolis, Ind. and were used according to the instructions from the manufacturers. Reverse transcriptase was obtained from Life Sciences, Inc., St. Petersburg, Fla. Media and media components were obtained from the Cell Culture Facility at the University of California, San Francisco, Calif. or from Gibco Laboratories, Grand Island, N.Y. Fetal bovine serum was obtained through HyClone Laboratories, Logan, Utah. Radioactive compounds were obtained from Amersham, Arlington Heights, Ill. Other materials were obtained as indicated below.

II. METHODS

A. RECOMBINANT DNA

Protocols for restriction endonuclease digestion, gel electrophoresis, plasmid DNA preparations, DNA fragment isolation and ligations were essentially as described in standard cloning manuals. See Maniatis, T. et al., *Molecular Cloning, A Laboratory Manual* (Cold Spring Harbor Press, New York (1982). Transformations of Escherichia coli DH-5 were peformed by the procedure described by Hanahan. See Hanahan, D., *J. Mol. Biol.* 166, 557 (1983).

B. PLASMID CONSTRUCTIONS 1. cTNT-CAT plasmids: The cloned cTNT gene, see Cooper, T. A. and Ordahl, C. P., *J. Biol. Chem.* 260, 11140 (1985), was truncated at nucleotide position +38 in exon 1 (all nucleotide positions are relative to transcription initiation site) by partial cleavage with Ava II followed by complete cleavage at an artificial Eco RI site located 3000 nucleotides upstream of the transcription initiation site. During the process of subcloning this segment into a pUC 8 polylinker the Ava II site was destroyed. The cTNT fragment was subsequently excised from this plasmid by Hind III digestion and cloned into the Hind III site of pBR-CAT, see Walkers M. D. et al., *Nature* 300, 557 (1983), to fuse the truncated cTNT untranslated region with the untranslated region of CAT via a polylinker. This plasmid is designated cTNT-3000 and served as the starting plasmid for creation of a nested set of 5' deletions as shown in FIG. 1. The 5' deletions were created by partial or complete digestion of cTNT-3000 at Pst I, Bgl II, Pvu II, Dde I, Hae III and Sma I sites located at nucleotide positions −1100, −550, −268, −201, −129, and −49, respectively. Restriction sites leaving overhanging ends were filled in with reverse transcriptase or digested with S-1 nuclease, and Hind III linkers added. Following digestion with Hind III the fragments were gel isolated and cloned into the Hind III site of pBR-CAT. The structure of each plasmid was confirmed by restriction endonuclease mapping or nucleotide sequencing, or both. These plasmids, designated cTNT-1100, −550, −268, −201, −129, −49, respectively, therefore share a common 3' end with cTNT-3000, but have varying amounts of upstream DNA deleted as indicated in FIG. 1. Since each deletion mutant was inserted into the same position of pBR-CAT, the upstream plasmid DNA sequences were identical for all constructions. To remove the cTNT TATA box and transcription initiation site, cTNT-129 and cTNT-268 were digested with Sma I, which cleaves at nucleotide position −49 and at a polylinker site downstream of position +38, and recircularized with T4 ligase. These clones are designated as cTNT-129[delta-49/+38] and cTNT-268[delta-49/+38] (see FIG. 1b).

2. Enhancer test constructions: The cTNT fragment from position −268 to −550 was isolated from cTNT-1100 by simultaneous digestion with Puv II and Bgl II. Hind III linkers were ligated to both ends after filling in the Bgl II site with reverse transcriptase. The fragment was cloned into the Hind III site of the pUC-based enhancer test plasmids pTE-2 S/N or pTE-2 which places the cTNT fragment either directly in front of the HSV tk promoter or at a position 600 bp upstream of the tk promoter, respectively, see Edlund, T. et al., *Science* 230, 912 (1985). orientation of the cTNT fragment with respect to the tk promoter was ascertained by restriction mapping.

3. bACT-275-CAT: The promoter region of the chicken beta-actin genet see Kosti T. A. et al., *Nucl. Acids Res.* 11, 8287 (1983), was isolated by partial digestion with Hpa II at position +61 within the first, untranslated exon, followed by complete cleavage at an Xho I site located at position −275. After addition of Hind III linkers as described above, the promoter fragment was gel isolated and inserted into the Hind III site of pBR-CAT. The structure of the fusion between beta-actin exon I and the CAT gene was confirmed by DNA sequencing and restriction endonuclease mapping.

C. PREPARATION OF CULTURED CELLS

1. Embryonic skeletal muscle cultures: Chicken day 11 embryo breast muscle tissue was dissected free of skin and cartilage and then dissociated either by mechanical means#see Caplan, A. I., *J. Embryol. Exp. Morphol.* 36, 175 (1976); Kongisberg, I. R., *Meth. Enzymol.* 58, 511 (1979), or by trypsinization, see Antin, P. B. et al., *J. Cell Biol.* 102, 1464 (1986), and then plated on gelatinized tissue culture plates at $1.5$-$10^6$ cells per 100 mm Corning tissue culture plate (American Scientific Products, McGaw Park, Ill.). Inclusion of 0.05% trypsin in 0.02% EDTA (STV) in the dissociation step did not affect the results presented here. The medium, consisting of Dulbecco's minimal essential medium (DMEM) supplemented with 10% horse serum (heat inactivated), 2.5% chicken embryo extract and 100 units per ml each of penicillin and streptomyocin was changed the day after plating, 3 hours prior to initiation of transfection.

2. Embryonic heart cell cultures: Heart cell cultures were prepared by method modified from established procedures, see DeHaan, R. L., *Devel. Biol.* 16, 216 (1967); Diugosz, A. A. et al., *J. Cell Biol.* 59, 2268 (1984); Kelly, A. M. and Chacko, S., *Devel. Biol.* 48, 421 (1976); Simpson, P. and Savion, S., *Circul. Res.* 50, 101 (1982); and Zadeh, B. J. et al., *Devel. Biol.* 115, 204 (1986). Briefly, hearts were excised from day 6 chicken embryos, dissected free of pericardia and great vessels under sterile conditions and then minced into small fragments. After rinsing in clean phosphate buffered saline (PBS), the tissue fragments were incubated in 10 ml of STV for 10 min at room temperature with gentle mixing. The supernatant from this was discarded and 7 mls fresh STV added. After an additional 8 minutes of digestion, the supernatant was transferred into a 50 ml Falcon tube containing 10 ml of ice-cold nutrient medium (5% fetal bovine serum, 100 units/ml of penicillin and streptomycin in M199 medium with Earles balanced salt solution). The remaining tissue was redigested as above for 3-4 additional cycles and the supernatants pooled. Liberated cardiac cells were collected by centrifugation at 2000 rpm for 10 min at 4° C., resuspended in nutrient medium and passed through a 20 uM mesh nylon screen to remove aggregates. Dissociated heart cells were plated at a density of $2.5 \times 10^6$ cells per 60 mm tissue culture plate. For histological studies, cells were cultured on rat tail collagen-coated aclar coverslips in 35 mm tissue culture plates. Cells were maintained in a 37° C humidified incubator with a 5% $CO_2$ atmosphere. Medium was changed the day after plating, 3 hours before initiating transfections.

3. Chicken embryo fibroblast cultures: Fibroblast cells were prepared from day 11 chicken embryos from which the head, viscera and appendages had been removed, see Rubin, 9., *Virology* 4, 533 (1957). After dissociation with STV, fibroblasts were grown in M199 medium supplemented with 10% tryptose phosphate, 10% fetal calf serum and 2% chicken serum. Primary fibroblast cultures were initially plated at $1.5 \times 10^6$ cells per 100 mm culture plate and were passaged at least three times (1:3 split) to remove myogenic cells prior to being used in transfection experiments. For transfection experiments, fibroblast cells were plated at $1.5 \times 10_6$ cells per 100 mm culture plate and the medium changed the day after elating, 3 hours prior to transfection.

D. IMMUNOFLUORESCENCE MICROSCOPY

The properties of the mouse monoclonal antibody prepared against bacterial chloramphenicol acetyltransferase (CAT) have been described, see Gorman, C., in 2 *DNA Cloning, a Practical Approach,* 143 (Glover, D. M. ed. IRL Press, Oxford, Washington, D.C. 1985). This antibody is highly specific for bacterial CAT and does not cross react with vertebrate cellular proteins. The rabbit antisera prepared against desmin binds to intermediate filaments in skeletal, cardiac, and smooth muscle but not bind to the vimentin intermediate filaments in fibroblasts, see Berner, P. et al., *J. Muscle Res. Cell Motil.* 2, 439 (1981) and Fellini, S. et al., *Am. J. Anat.* 153, 451 (1978).

For double label immunofluorescence analysis of transfected cells, cultures were rinsed with PBS fixed for 5 min at room temperature in 4% formaldehyde in PBS. The cells were then rinsed twice briefly with PBS and coverslips placed in ice cold methanol for 4 min followed with ice cold acetone for 2 min. Cells were then immediately rehydrated in PBS and washed three times for a total of 15 min with PBS. To stain cells simultaneously with the rabbit polyclonal anti-desmin (gift of H. Holtzer, University of Pennsylvania, Pa. and ICN Nutritional Biochemicals, Cleveland, Ohio) and mouse monoclonal anti-CAT (gift of C. Gorman, Genentech Corp., South San Francisco, Calif.), coverslips were incubated simultaneously with the appropriate dilution of each antibody in a humid chamber at 37° C. for 1 hour, washed three times for a total of 30 minutes with PBS, and subsequently incubated with a 1:200 dilution each of rhodamine-labelled goat anti-mouse IgG and fluorescein-labelled goat anti-rabbit IgG (Cappell Laboratories, Cochranville, Pa.) in a humid chamber at 37° C. for 1 hour. For some experiments, following primary antibody incubation and washing, CAT antibody was visualized by incubating cells with a 1:200 dilution of biotinylated horse anti-mouse IgG (Amersham) for 1 hour at 37° C., followed by a 1:200 dilution of Texas Red-conjugated streptavidin (Amersham) at room temperature for 30 minutes. Cells were then washed three times for a total of 30 minutes with PBS, dehydrated in a graded ethanol series and mounted in Mowiol. In some preparations, the DNA binding fluorochrome DAPI (Sigma Chemical Company, St. Louis, Mo.) was used to visualize nuclei. Cells were examined with either a Leitz or a Zeiss epifluorescence microscope using the appropriate filters to selectively visualize fluorescein, rhodamine or Texas Red fluorescence.

Purity of the muscle cultures was monitored immunochemically to establish the fraction of muscle and non-muscle cells at various times after plating. For skeletal muscle cells, 75% to 90% of the nuclei in skeletal muscle cultures resided in desmin-positive cytoplasm even after 72 hours in culture. Heart cell cultures are 70–80% cardiac myocytes 24 hours after plating; however, after 72 hours in culture, the proportion of cardiac myocytes dropped to 50–60%. Based on incorporation of $^3$H-thymidine, this shift was apparently due to the lower mitotic rate of myocardial cells than nonmyocardial cells in culture because, over a 48 hour period, only 17% of myocardial cells showed nuclear incorporation of $^3$H-thymidine, as compared to 66% for nonmyocardial cells.

E. CELL TRANSFECTION

Twenty-four hours after cell plating the medium was changed and three hours later the cells were transfected with DNA-calcium phosphate precipitates in accordance with known procedures, see Graham, F. and van der Eb, A., *Virology* 52, 456 (1973), and Gorman, C. M. et al., *Mol. Cell Biol.* 2, 1044 (1983), using 10 ug of plasmid DNA which has been purified by banding twice on cesium chloride-ethidium bromide density gradients. After four hours at 37° C., the medium containing the DNA precipitate was removed; cells were washed with 10 ml of serum-free medium and then treated with 1 ml of 15% glycerol in a HEPES (N-2-hydroxylpiperazin-N'-2-ethanesulfonic acid)-buffered sodium phosphate solution for 10 seconds (muscle cells) or 30 seconds (fibroblast cells) at room temperature, see Gorman, C. M. et al., *Mol. Cell Biol.* 2, 1044 (1983). The glycerol solution was removed and the cells were washed with 10 ml of serum-free medium and then incubated with 10 ml of complete medium at 37° C. for 48 hours. Transfection of DNA into cardiac cell cultures was carried out as described above except that the transfection cocktail/medium mixture was left on the cells for 6 hours, after which it was removed and the cells rinsed once with fresh nutrient medium and then glycerol shocked for 30 seconds.

Several measures were taken to ensure that CAT activity differences among promoters are not due to transfection variability. First, all comparisons are based on data collated from at least six separate experiments, except in a few cases where noted. Second, all constructions to be compared were transfected simultaneously in each experiment onto duplicate or triplicate plates. The differences observed were reproducible from experiment to experiment. Third, the same DNA-calcium phosphate transfection cocktail was applied both to muscle and fibroblast cultures within each experiment. Fourth, different preparations of each plasmid construction were used in parallel experiments. These last two measures were taken to rule out either transfection cocktail or plasmid DNA preparation as potential sources of the differences observed. Using these procedures, the standard error of the means (SEM), in most cases, is less than 10% of the observed signal. Experiments using co-transfection of a second control plasmid, see Walker, M. D., *Nature* 300, 557 (1983), showed competitive interference between the control promoters and the cTNT promoters. This was due to a property inherent in the cTNT promoter because co-transfection of RSV-Beta-galactosidase, see Walker, M. D., *Nature* 300, 557 (1983), did not interfere with expression of the HSV tk promoter in the cell systems reported here. In experiments using the RSV-Beta-galactosidase as the control plasmid, the mean corected level of CAT activity directed by the HSV tk promoter and the SEM were essentially identical to that obtained when the above precautions were taken. Both methods gave activity values with SEM of less than 10% indicating that both procedures gave quivalent results.

The activity differences among constructions were also analyzed by statistical methods. The data were subjected to a 2-way analysis of variance, or an analysis of variance for repeated samples, using CRUNCH statistical software (CRUNCH Softwares, Oakland, Calif.) to determine whether the CAT activity values determined for any two constructions were statistically different. Promoter activities were considered different only when the confidence level is within $P=0.01-0.05$.

F. CAT ASSAY

Cell extracts were prepared by sonication and centrifugation, see Gorman, C. M., *Mol. Cell Biol.* 2, 1044 (1983), and CAT activity was assayed using $^{14}$C-chloramphenicol, see Gorman, C. M., *Mol. Cell Biol.* 2, 1044 (1983), and Walker, M. D., *Nature* 300, 557 (1983). The amount of extract employed was varied to ensure that CAT activity was measured within the linear range. The linearity of the CAT assay reaction was determined empirically. Reaction products were separated by ascending chromatography on silica gel plates using chloroform-methanol (90:10 v/v). Following autoradiography, acetylated and unreacted $^{14}$C-chloramphenicol were quantified by liquid scintillation counting.

III. RESULTS

A. CONSTRUCTION OF cTNT-CAT FUSION GENES

Figure 1B:
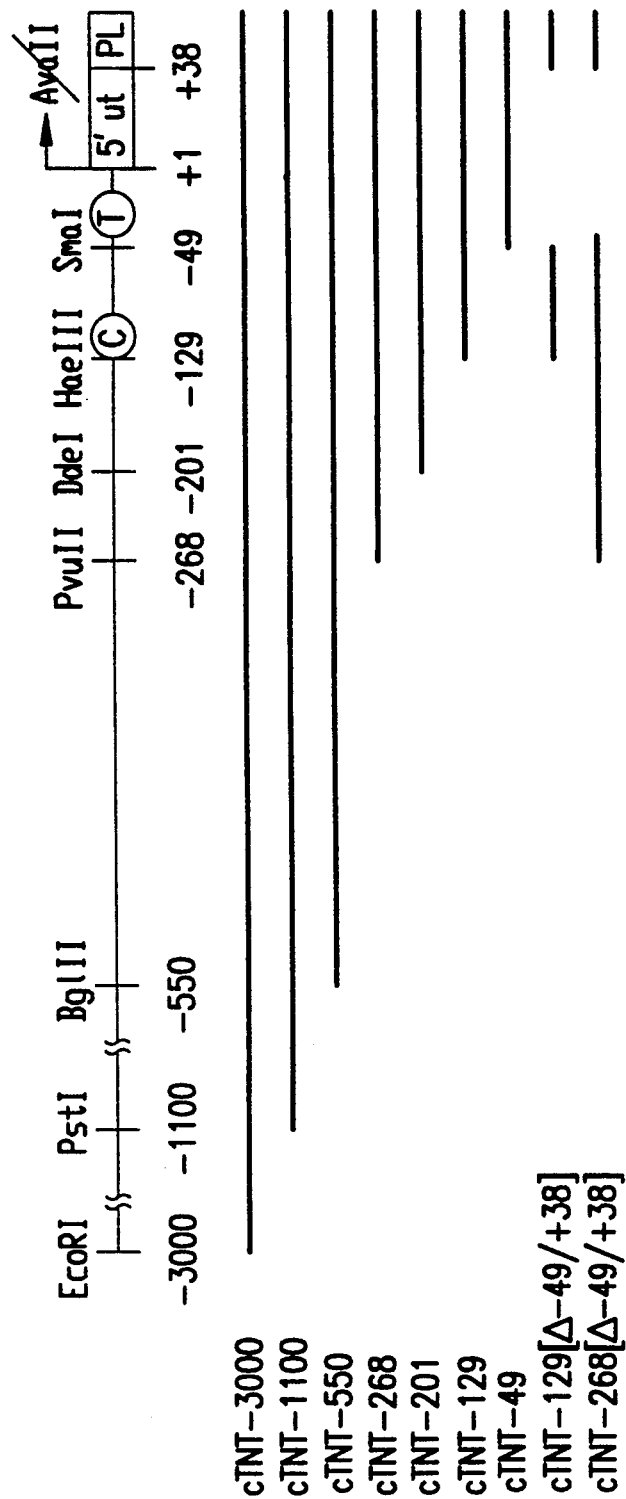
Figure 1C:
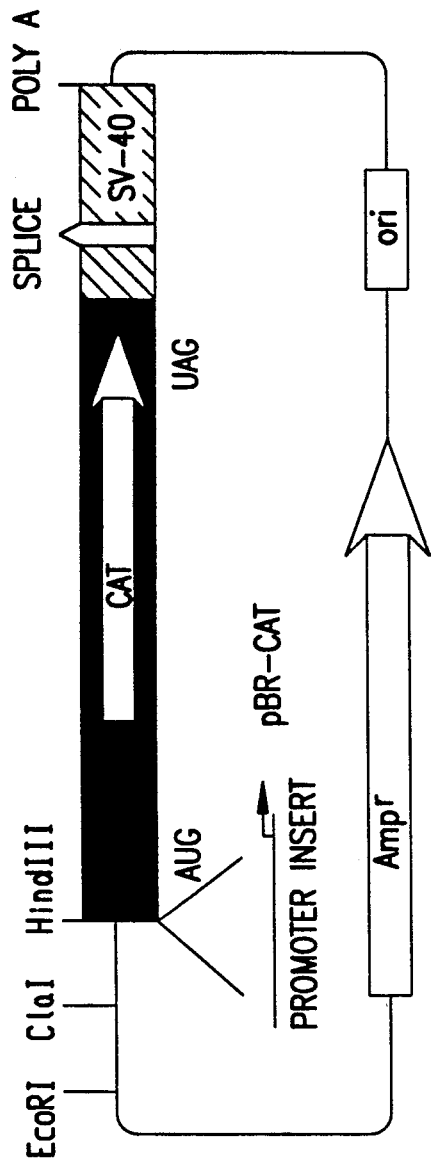

The overall structure of the chicken cTNT gene, as shown in FIG. 1a, was determined by nucleotide sequencing of the cloned gene, see Cooper, T. A. and Ordahl, C. P., *J. Biol. Chem.* 260, 11140 (1985). The promoter/upstream region of the cloned cTNT gene was isolated by partial digestion at an Ava II restriction endonuclease cleavage site located 38 nucleotides into exon 1, and an artificial Eco RI site located 3 thousand bases (kilobases, kb) upstream (FIG. 1b). This cTNT promoter/upstream segment was then cloned into the Hind III site of pBR-CAT (FIG. 1c). This construction (cTNT-3000) fuses the cTNT untranslated first exon to the untranslated region of the CAT gene, and places the transcription of the CAT gene under control of the cTNT promoter and transcription initiation site. Progressive deletions from the 5' end of cTNT-3000 were made by partial or complete digestion at convenient restriction endonuclease cleavage sites (FIG. 1b). Each deletion segment was then cloned into the Hind III site located upstream of the CAT gene in pBR-CAT (see FIG. 1C and Methods). This created a nested set of cTNT promoter/upstream deletion mutants which had identical 3' endpoints in exon 1 and identical 5' flanking vector sequences, but which lacked varying amounts of upstream DNA as diagrammed in FIG. 1b.

B. TRANSFECTION OF cTNT-CAT FUSION GENES INTO EMBRYONIC SKELETAL MUSCLE CULTURES

Mononucleated myoblasts from day 11 chicken embryos were plated at $1.5 \times 10^6$ cells per 100 mm plate and cultured using standard procedures. After approximately 48 hours in culture, the mononucleated myoblasts fuse to form differentiated, multinucleated myotubes. For transfection experiments, a calcium phosphate precipitate containing 10 ug plasmid DNA was introduced into cultures 24 hours after plating, when the level of myocyte differentiation is very low. Forty-eight hours after transfection, the well-differentiated muscle cultures were harvested for determination of the level of CAT expression. Thus#the greatest proportion of cells taking up plasmid DNA at the time of transfection were undifferentiated myoblasts, but by the time of harvest, the majority of these transfected cells had differentiated. Therefore, the CAT activity detected was attributable to expression within differentiated myotubes. This conclusion is further supported by immunocytochemical analyses described below.

Each of the cTNT deletion mutants shown in FIG. 1b was transfected into embryonic skeletal muscle cultures and the resulting CAT activity determined. Table 1 shows the collated data from at least six independent experiments for each deletion mutant. Multiple experiments using triplicate samples and at least two different DNA preparations were used to control for transfection efficiency. Co-transfection of control markers with the cTNT-CAT constructions resulted in competition between the cTNT test promotor and control promoters. To ensure consistency between experiments, all the constructions were transfected simultaneously and control constructions (pBR-CAT, RSV-CAT and bACT-275-CAT) were included in every experiment (for details, see Methods).

One of the primary goals of these experiments was to determine the minimum amount of upstream DNA required for activity of the cTNT promoter in embryonic skeletal muscle cells. Table 1 shows that cTNT-129 directs a high level of CAT expression in embryonic skeletal muscle cells. cTNT-129 contains many of sequence motifs expected for eucaryotic promoters, including putative TATA, SP-1 and CCAAT homologies, 38 nucleotides of exon 1, as well as two copies of the heptamer CATTCCT which is found in many contractile protein gene promoter regions (see FIG. 2; see generally Cooper, T. A. and Ordahl, C. P., *J. Biol. Chem.* 260, 11140 (1985); Nikovits, W. et al., *Nucl. Acid Res.* 14, 3377 (1986). Deletion to position −49 (cTNT-49, FIG. 1), leaving only the proximal segment containing the putative TATA motif and exon 1 sequence (FIG. 2), reduces CAT activity to a basal level comparable to pBR-CAT which lacks a eucaryotic promoter (Table 1). Similarly, the cTNT, promoter is inactive in the absence of the proximal segment, between positions −49 and +38 (Table 1). These internal deletion experiments indicate that both the proximal and the distal segments of cTNT-129 appear to be required for activity in skeletal muscle cells.

TABLE 1

PROMOTER ACTIVITY IN MUSCLE AND NON-MUSCLE CELLS[1]

| Promoter | Units ($\times 10^{-2}$) CAT Activity In: | | |
|---|---|---|---|
| | Skeletal myocytes | Cardiac myocytes | Fibroblast cells |
| cTNT-3000 | 15.0 ± 3.0 | 1.04 ± 0.28 | 0.28 ± 0.02 |
| cTNT-1100 | 46.0 ± 6.0 | 1.49 ± 0.51 | 0.31 ± 0.03 |
| cTNT-550 | 90.0 ± 7.0 | 4.07 ± 1.04 | 0.18 ± 0.02 |
| cTNT-268 | 17.0 ± 2.0 | 1.41 ± 0.16 | 0.30 ± 0.03 |
| cTNT-201 | 15.0 ± 3.0 | 0.24 ± 0.11 | 0.33 ± 0.03 |
| cTNT-129 | 26.0 ± 3.0 | 0.17 ± 0.08 | 0.36 ± 0.04 |
| cTNT-129 | 26.0 ± 3.0 | 0.17 ± 0.08 | 0.36 ± 0.04 |
| cTNT-49 | 0.16 ± 0.05 | 0.14 ± 0.03 | 0.14 ± 0.05 |
| cTNT-129 [delta-49/+38] | 0.16 ± 0.05 | 0.09 ± 0.06 | 0.07 ± 0.03 |
| cTNT-268 [delta-49/+38] | 0.13 ± 0.05 | 0.16 ± 0.04 | 0.11 ± 0.02 |
| Beta-Actin | 90.0 ± 4.0 | 6.6 ± 0.98[2] | 139 ± 14 |
| RSV LTR | 305 ± 108 | 20.9 ± 4.3[2] | 693 ± 39 |

[1]The CAT activity values shown are the average of a minimum of six determinations, except for that of cTNT-49, and cTNT-129 [delta-49/+38] for which only three determinations were made. The standard error of the mean is given in each case. The activity of pBR-CAT (0.44 ± 0.13; 0.28 ± 0.08 and 0.24 ± 0.04 for skeletal myocytes, cardiac myocytes and fibroblast cells, respectively) was subtracted from each value indicated.
[2]As described in the text, the values shown for the beta-actin (bACT-275) and RSV LTR promoters in cardiac myocytes have been corrected to account for the fractional contribution of CAT activity derived from cardiac myocytes to the overall activity in these samples, determined as in Table 2. The uncorrected values for the beta-actin and RSV LTR promoters in heart cell cultures were 49.6 ± 7.4 and 158 ± 33, respectively.

In addition to defining an approximate minimum promoter region, the results with the nested set of upstream deletions indicate that the presence of regions upstream of the −129 position can affect the overall level of activity of the cTNT minimum promoter. Inclusion of the region between positions −268 and −129 (cTNT-201, and cTNT-268, Table 1) has little effect upon activity. However, additional inclusion of the −550 to −269 segment results in a 3-fold increase in the level of CAT expression (cTNT-550, Table 1). Inclusion of additional upstream DNA (cTNT-1100 and cTNT-3000; Table 1) results in diminution of the level of CAT expression. These effects of upstream regions could be due to the presence of positive and negative regulatory elements or to effects of spacing between the cTNT promoter and plasmid vector sequences. For the purposes of the present application, these regions have been designated "regulatory regions" for convenience in describing their functional effects.

Figure 3A:
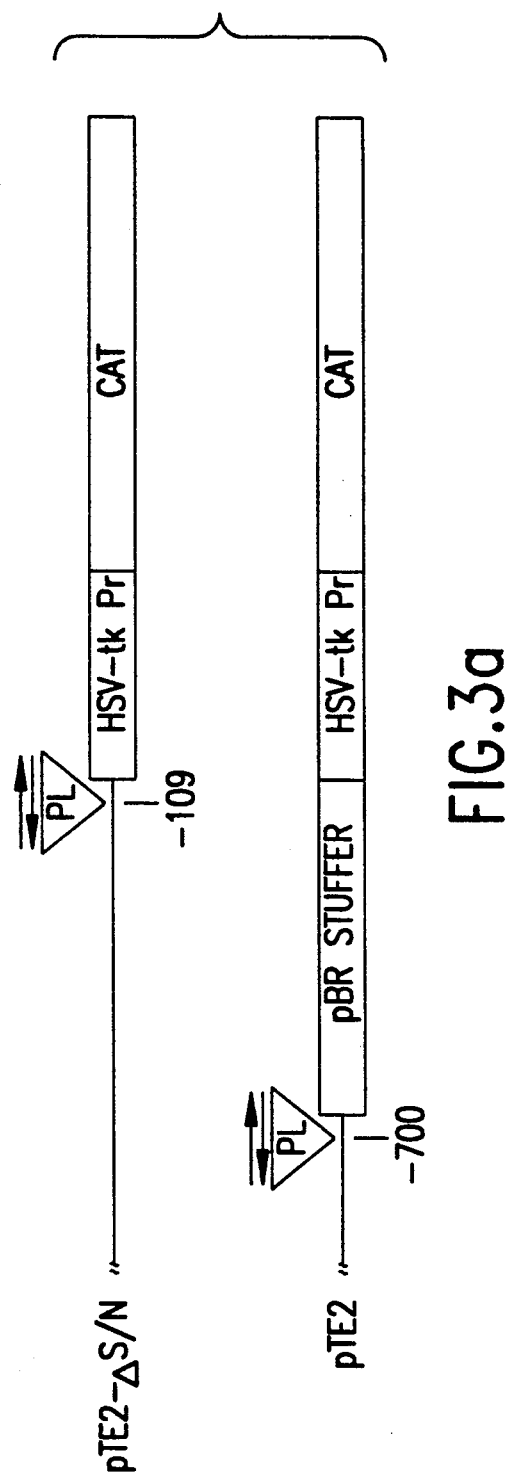
Figure 3B:
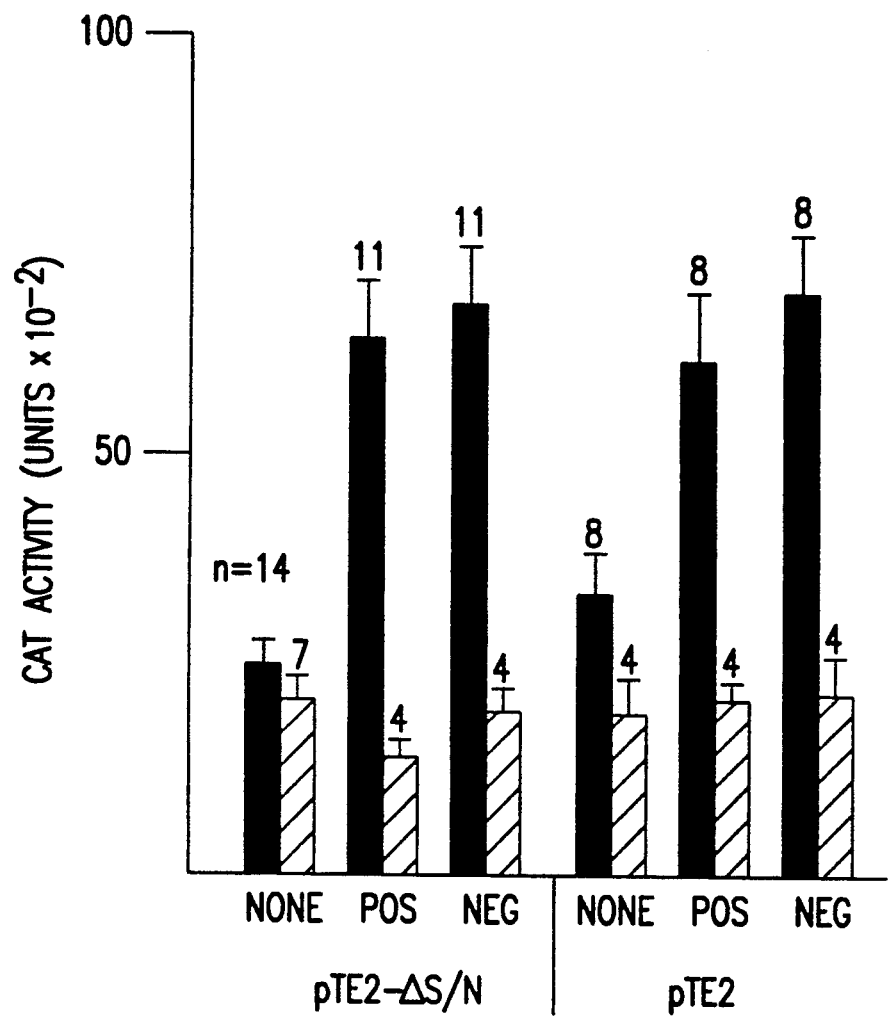
Figure 3C:
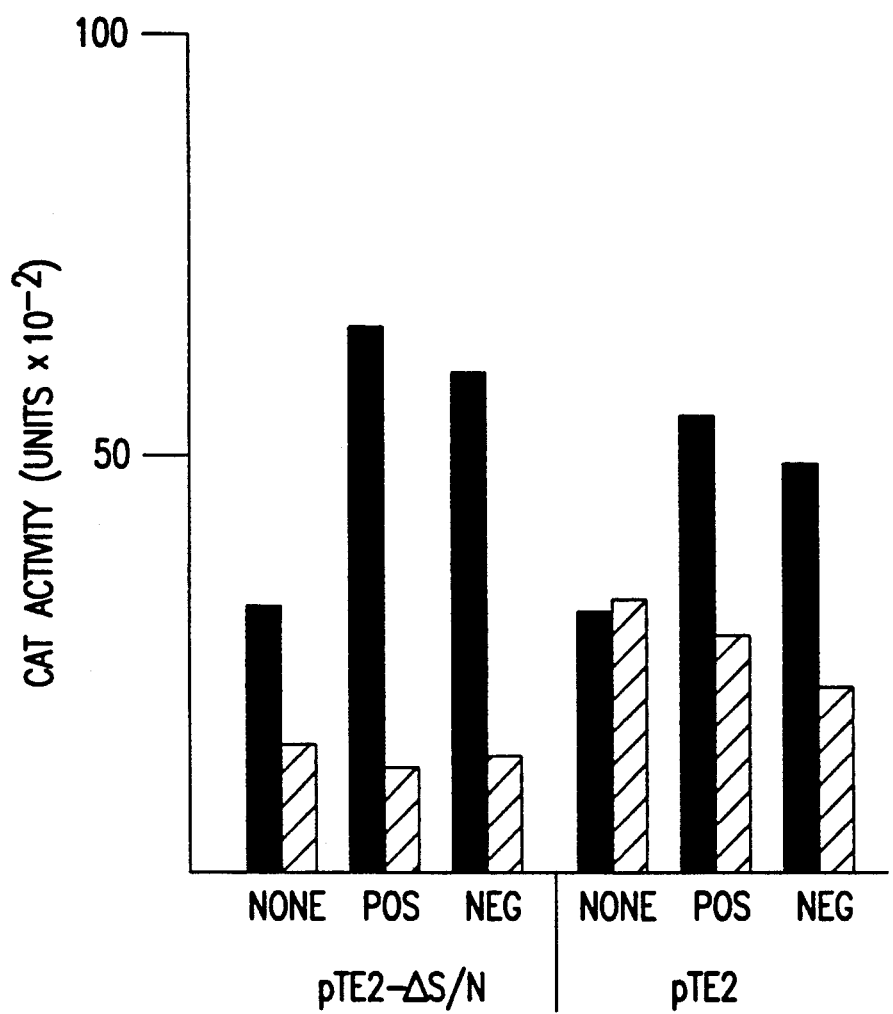

In order to determine if the apparent positive effect of the −550/−269 region could act independent of surrounding sequences, we tested its ability to affect CAT expression under the control of a heterologous promoter. For these experiments we used a series of pUC-based plasmids designed for testing potential enhancer-containing DNA segments. Test sequences may be inserted into a polylinker located either at a distal site 600 nucleotides upstream (pTE-2), or a proximal site immediately upstream (pTE-2 S/N) of the Herpes simplex virus thymidine kinase (HSV tk) gene promoter. See Edlund, T., et al., *Science* 230, 912 (1985). The level of CAT activity expressed under control of the HSV tk promoter in the plasmids carrying a test segment was then compared to that of the parent plasmid. The −550/−269 segment was excised and cloned into these two plasmids via linkers in both orientations (FIG. 3a). FIG. 3b shows that the presence of the −550/−269 segment increased expression of CAT under control of the HSV tk promoter approximately 2- to 3-fold in skeletal muscle cultures, in an orientation- and position-independent manner. Little or no potentiation was observed after transfection into fibroblast cultures (FIG. 3b). Unlike the cTNT promoter, the HSV tk promoter was found to be minimally affected by the presence of a co-transfection marker. Using RSV-beta-galactosidase as a co-transfected marker to control for transfection efficiency the preferential potentiation of CAT activity in muscle cells transfected with test plasmids containing the −550/−269 segment was also evident (FIG. 3c). Thus, the level of the potentiation of CAT expression from the HSV tk promoter by the −550/−269 segment is similar to that observed when it is present in its normal position upstream of the cTNT promoter.

C. TRANSCRIPTIONAL STRENGTH OF THE cTNT PROMOTER IN SKELETAL MUSCLE CELLS

Figure 1D:
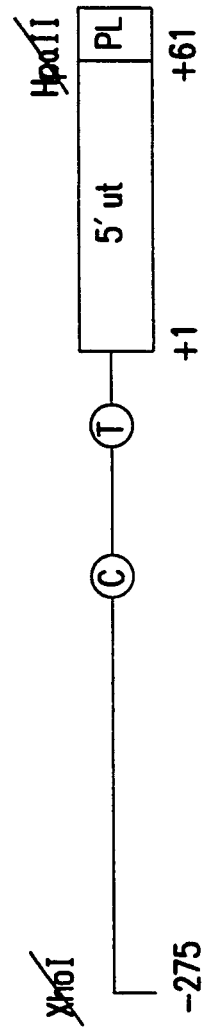

The transcriptional strength of the cTNT promoter/upstream segments in skeletal muscle cells was estimated by comparing CAT activity governed by each of them to that directed by two control promoters/ those of the Rous sarcoma virus long terminal repeat (RSV-LTR) and the chicken beta-actin gene (bACT-275, see FIG. 1d). Both of these promoters are strong chicken promoters which are active in a wide variety of cell types. See Fregien, N. and Davidson, N., *Gene* 48, 1 (1987) and Gorman, C. M. et al., *Proc. Natl. Acad. Sci. U.S.A.* 79, 67777 (1982). The construction of RSV-CAT has been described. See Gorman, C. M. et al., *Proc. Natl. Acad. Sci. U.S.A.* 79, 67777 (1982). The bACT-275 plasmid contains the DNA segment between −275 and −40 relative to the site of transcription initiation in the chicken beta-actin gene (see FIG. 1d). Although the endogenous beta-actin gene is down-regulated in differentiated muscle cells in vivo, we found the activity of bACT-275-CAT was similar in transfected skeletal muscle and fibroblast cells (Table 1). Thus, the cis sequences required for beta-actin gene down regulation do not appear to be present (or active) on the segment we have isolated, so bACT-275-CAT serves as a good cell type non-specific control promoter in these experiments. The level of CAT expression under control of the bACT-275 was equivalent to that under control of cTNT-550, the strongest cTNT promoter upstream segment (Table 1). Both of these cellular promoters were approximately one-third as active as the RSV-LTR (Table 1). Since the RSV-LTR is one of the strongest known viral promoters, see Gorman, C. M. et al., *Proc. Natl. Acad. Sci. U.S.A.* 79, 6777 (1982); and Walker, M. C., *Nature* 300, 557 (1983), and is stronger than any known cellular promoter, we conclude that both cTNT-550 and bACT-275 are strong cellular promoters in skeletal muscle cells.

The site of transcription initiation from the transfected cTNT and RSV promoters was determined by primer extension using an oligonucleotide primer complementary to codons 6-11 of CAT mRNA. See Walkert M. D., *Nature* 300, 557 (1983). RNA from cultures transfected with RSV-CAT gave a primer extension run-off length of 109 nucleotides indicating that CAT mRNAs governed by the RSV promoter were initiated at the expected site. See FIG. 4; Walker, M. D., *Nature* 300, 557 (1983). RNA from cultures transfected with cTNT-550-CAT yielded two predominant run-off lengths of 141 and 145 nucleotides (FIG. 4), indicating that initiation occurred at the first and fifth nucleotides of cTNT exon 1. This double initiation signature is characteristic of cTNT transcription initiation, see FIG. 2; Cooper, T. A. and Ordahl, C. P., *J. Biol. Chem.* 260, 11140 (1985), and indicates that the transcription initiation from the transfected gene mimics that of the endogenous gene. The relative level of correctly initiated CAT mRNA under control of the cTNT and RSV promoters was estimated by densitometry scanning of the films to be 0.2, in good agreement with the relative level of CAT activity of 0.3 specified by the two promoters (Table 1).

D. TRANSFECTION OF cTNT-CAT FUSION GENES INTO EMBRYONIC HEART CELL CULTURES

Heart cell cultures were established using cells dissociated from day six and day ten embryo hearts. Cultures from day six embryo hearts were chosen for the experiments reported below because they were found to be more easily transfected than those from day ten embryos. Results with heart cell cultures from either age embryo were, however, qualitatively identical. The optimum schedule for transfection of myocardial cultures was found to be the same as that for skeletal muscle cultures; i.e., cells were transfected 24 hours after plating and harvested for CAT activity 48 hours later. Myocardial cell cultures were less homogeneous, in terms of the proportion of myogenic cells, than skeletal muscle cultures. Immunocytochemical analysis showed that approximately 80% of the nuclei resided in cytoplasm binding antibody against the muscle specific intermediate filament protein, desmin, after 24 hours in culture. However, after 72 hours in culture the proportion of desmin-positive cells and decreased to 50-60%. This change was attributable to a higher rate of cell division for non-myocardial cells as demonstrated by a four-fold higher rate of thymidine incorporation (see Methods).

The transfection efficiency of myocardial and non-myocardial cell types within embryonic heart cell cultures was also found to differ. Using a monoclonal antibody for CAT protein, see Gorman, C. in 2 *DNA Cloning, a Practical Approach,* 143 (Glover, D. M. ed. 1985), transfected cells could be detected immunocytochemically. Table 2 shows that in heart cell cultures transfected with RSV-CAT, an average of 6.5 times more non-myocardial (desmin-negative) cells were CAT-positive than myocardial cells (desmin-positive). Thus, the overall transfection efficiency of myocardial cells is much lower than that of non-myocardial cells. These immunofluorescent data indicate, as a first approximation, that of the total CAT activity directed by the RSV-LTR or beta-actin promoters measured in transfected heart cell cultures, only one part in 7.5 attributable to activity in myocardial cells (see footnote to Table 1). The lower levels of CAT activity for heart cultures versus skeletal muscle cultures (Table 1), therefore, reflect the lower percentages of myogenic cells transfected in heart cultures. Skeletal muscle and fibroblast cultures were transfected with similar efficiency (approximately 2%, data not shown).

TABLE 2

| IMMUNOCYTOCHEMICAL ANALYSIS OF TRANSFECTION EFFICIENCY IN HEART CELL CULTURES[1] | | | |
|---|---|---|---|
| | Number of CAT-Positive Cells Staining | | |
| Experiment # | Desmin-Positive | Desmin-Negative | Ratio |
| 1 | 28 | 202 | 11.3 |
| 2 | 36 | 121 | 4.3 |
| 3 | 80 | 337 | 4.6 |
| | | Avg | 6.5 |

[1]Heart cell cultures established on aclar coverslips in 35 mm dishes were transfected 24 hours after plating, essentially as described in Methods. Forty-eight hours after transfection, the cells were processed for immunocytochemistry as described in Methods. Every CAT-positive cell on a 22 mm² aclar coverslip was determined and assayed for staining with anti-desmin. The percentage of desmin-positive cells was then determined for each experiment to allow normalization of the relative number of myocardial and non-myocardial cells for determination of relative transfection efficiency (Ratio). The fraction of desmin-positive cells was 0.61, 0.56 and 0.52 for experiments 1, 2, and 3, respectively. Each transfection experiment was conducted independently by a separate operator and the immunocytochemical counting performed by a fourth operator.

Table 1 shows the CAT activity levels specified by each member of the set of cTNT deletions after transfection into heart cell cultures. These results indicate that the shortest deletion mutant which is active in cardiac cells contains 268 upstream nucleotides (see FIG. 2 for nucleotide sequence). Deletion to position −201 essentially abolishes CAT activity under control of the cTNT promoter, reducing it to a level comparable to the promoterless pBR-CAT (see Table 1). Similarly, cTNT-129, which was strongly active in skeletal muscle cells, is also inactive in cardiac cells. Thus, the upstream segment between positions −268 and −201 appears to be required for a significant level of cTNT promoter activity in cardiac cells.

The region between −550 and −269, while not required for activity, also increases the level of CAT expression under control of the cTNT promoter in cardiac cells by approximately three-fold, in a manner similar to its effect in skeletal muscle cells. In addition, the regions upstream of position −550 appear to suppress the maximal activity of the cTNT promoter similar to the effect of this region in skeletal muscle cells. Therefore, the effects of upstream regions upon activity of the minimum cTNT promoter in both cardiac and skeletal muscle appear to be similar.

The transcriptional strength of the cTNT promoter in cardiac myocytes was also evaluated by comparison to that of the RSV-LTR and beta-actin promoters. As indicated above, the beta-actin and RSV-LTR promoters are preferentially expressed in non-myocardial cells owing to a difference in transfection efficiency. Since the cTNT promoter was only expressed in myocardial cells (see below), the measured level of CAT activity directed by each of the cTNT constructions was directly comparable to that of the corrected values of the beta-actin and RSV-LTR promoters as shown in Table 1. Using this comparison, the activity of cTNT-550 is approximately equivalent to that of the beta-actin promoter in cardiac muscle cells. Thus, the relative strength of cTNT-550 appears to be approximately equivalent in embryonic cardiac and skeletal muscle cells. The low efficiency of transfection of myocardial cells precluded using primer extension to determine the transcription initiation site of the transfected cTNT promoter. However, the site of transcription initiation from the endogenous cTNT gene is identical in embryonic cardiac and skeletal muscle cells, see Cooper, T. A. and Ordahl, C. P., *J. Biol. Chem.* 260, 11140 (1985), so there is no a priori reason to suggest that the transfected cTNT gene would use a different site in cardiac muscle cultures than in skeletal muscle cultures. In addition, deletion of the −49 to +38 region of cTNT-268 (which contains the putative TATA motif, transcription initiation sites and exon 1; see FIG. 2) abolishes activity in cardiac cells (cTNT-268 [delta-49+38]; Table 1), which is also consistent with expression being dependent upon transcriptional initiation at the natural cTNT sites.

E. CELL-SPECIFICITY OF THE cTNT PROMOTER

The cell specificity of the cTNT and control promoters was assessed by comparing the level of CAT expression in skeletal or heart muscle cells to that in fibroblast cells. Chicken embryo fibroblasts were prepared and cultured under standard conditions and passaged at least three times before use in transfection experiments to eliminate potentially myogenic cells. Fibroblast cultures were transfected 24 hours after plating and harvested 48 hours later. In most cases, the same transfection cocktail was simultaneously applied to fibroblast cultures and to myogenic cultures.

While both the beta-actin and RSV-LTR promoters were found to be highly active in fibroblast cells, the activity of the cTNT promoter/upstream segments was extremely low in these cells (Table 1). The activity of the cTNT promoter/upstream segments was only approximately two-fold higher than that of pBR-CAT, which lacks a eucaryotic transcriptional promoter (Table 1). Thus, the cTNT promoter appears to be essentially inactive in fibroblast cells regardless of the amount of upstream DNA present. The degree of cell specificity of each cTNT deletion mutant was estimated by comparing its level of CAT expression to that of the non-cell-specific bACT-275-CAT in each cell type (Table 3). These results indicate that the minimum cTNT promoter in cardiac and skeletal muscle cells is approximately two-order of magnitude more active than it is in fibroblasts (Table 3). With addition of the −550/−269 region, the overall level of cell specificity increases to almost three-orders of magnitude for both cell types. Thus, by these criteria, the cTNT promoter appears to carry cis elements directing a high degree of striated muscle specific transcription.

TABLE 3

RELATIVE ACTIVITY OF cTNT PROMOTER SEGMENTS IN MUSCLE AND NON-MUSCLE CELLS[1]

| Promoter | Activity Relative to b-Actin in: | | | Activity Ratio[2] | |
|---|---|---|---|---|---|
| | Skeletal myocytes | Cardiac myocytes | Fibroblast cells | Sk/F | Ca/F |
| cTNT-3000 | 0.167 | 0.158 | 0.0020 | 83 | 79 |
| cTNT-1100 | 0.511 | 0.226 | 0.0022 | 229 | 102 |
| cTNT-550 | 1 | 0.617 | 0.0013 | 772 | 478 |
| cTNT-268 | 0.189 | 0.214 | 0.0022 | 88 | 99 |
| cTNT-201 | 0.167 | 0.036 | 0.0024 | 70 | — |
| cTNT-129 | 0.289 | 0.026 | 0.0026 | 112 | — |
| cTNT-49 | 0.0018 | 0.021 | 0.0010 | — | — |
| cTNT-129 [delta-49/+38] | 0.0018 | 0.014 | 0.0005 | — | — |
| Beta-Actin | 1 | 1 | 1 | 1 | 1 |
| RSV LTR | 3.39 | 3.2 | 5.0 | 1 | 1 |

[1]Using the data from Table 1, the activity of the beta-actin promoter in each cell type was set at unity, and the relative activities for all other constructions calculated relative to that.
[2]The ratio of activity for each construction in skeletal myocytes versus fibroblast cells (Sk/F) and cardiac myocytes versus fibroblast cells (Ca/F). Ratio values are rounded off to the nearest whole number, and are omitted where only nominal activity was detected in skeletal or cardiac myocytes.

The cell specificity of the cTNT promoter in skeletal and cardiac muscle cells was also analyzed by immunocytochemistry. Cardiac and skeletal muscle cultures, grown on coverslips, were transfected with either RSV-CAT or cTNT-CAT and, after 48 hours, were fixed and incubated simultaneously with anti-desmin and anti-CAT, as in Table 2. As noted elsewhere, see Gorman, C., in 2 *DNA Cloning, A Practical Approach*, 143 (Glover, D. M. ed. 1985), CAT staining was observed both within the cytoplasm and nuclei. Desmin staining was restricted to intermediate filaments in the cytoplasm of muscle cells.

The total number of CAT-positive cells which were either desmin-positive (cardiac or skeletal myocytes) or desmin-negative (non-myocyte) was then determined as in Table 2. After transfection with RSV-CAT both desmin-positive and desmin-negative cells stained positively for CAT in cardiac (Table 4) and skeletal muscle cultures (Table 5) indicating that the RSV promoter is active in all three cell types. The relative number of CAT-positive non-myocytes is low in skeletal muscle cultures (Table 5), owing to the relative scarcity of these cells in these cultures (see Methods). The relative efficiency of transfection of myocytes and non-myocytes appears to be approximately equivalent in embryonic skeletal muscle cultures (see footnote to Table 5). However, in heart muscle cultures transfected with RSV-CAT (Table 4), the proportion of CAT-positive non-myocytes is higher owing to the higher relative number of non-myocardial cells, and their higher degree of transfectability, in agreement with the data present in Table 2.

TABLE 4

IMMUNOCYTOCHEMICAL ANALYSIS OF CARDIAC SPECIFIC EXPRESSION OF THE cTNT PROMOTER[1]

| Promoter | Number of CAT-Positive Cells Staining | |
|---|---|---|
| | Desmin-Positive | Desmin-Negative |
| RSV | 38 | 220 |
| cTNT | 40 | 0 |

[1]Immunocytochemical analysis of cardiac cell cultures which had been transfected with cTNT-CAT or RSV-CAT was conducted essentially as described in Table 2. The fraction of desmin-positive cells in cultures transfected with RSV-CAT and cTNT-CAT were 0.5 and 0.52, respectively.

TABLE 5

IMMUNOCYTOCHEMICAL ANALYSIS OF SKELETAL MUSCLE SPECIFIC EXPRESSION OF THE cTNT PROMOTER[1]

| Promoter | Number of CAT-Positive Cells Staining | |
|---|---|---|
| | Desmin-Positive | Desmin-Negative |
| RSV | 429 | 33 |
| cTNT | 533 | 0 |

[1] Muscle cell cultures were transfected 24 hours after plating, and processed for immunocytochemistry as described in Table 2 and in Methods. The total number of CAT-positive cells on a 22 mm$^2$ aclar coverslip was counted and each assayed for staining with anti-desmin. Each desmin-positive/CAT-positive cell was counted as a single cell regardless of the number of nuclei present on the assumption that only one transfected nucleus was presented per myotube. At the time point chosen approximately 70-90% of the cells in these cultures stain positively with anti-desmin, similar to control, non-transfected cultures. Since the relative transfection efficiency of muscle and non-muscle cells appears to be approximately equal in these cultures, no correction for the relative number of desmin-positive and desmin-negative cells has been made.

When transfected with cTNT-550-CAT, on the other hand, only desmin-positive cells were observed to be CAT positive either in embryonic heart cell cultures (Table 4) or in embryonic skeletal muscle cultures (Table 5). In the thousands of cells screened by this procedure, no CAT-positive/desmin-negative cells have ever been observed after transfection with cTNT-CAT. These results corroborate those based upon biochemical determination of CAT activity and indicate that the expression of the cTNT promoter/upstream segments tested here is highly specific for the same two striated muscle cells types to which it is restricted in vivo.

IV. DISCUSSION

In these experiments, we have used the chloramphenicol acetyltransferase (CAT) marker gene, see Gorman, C. M. et al., *Proc. Natl. Acad. Sci. U.S.A.* 79, 6777 (1982), and Gorman, C. M. et al., *Mol. Cell Biol.* 2, 1044 (1983), to analyze the transcriptional activity of the cTNT promoter/upstream region after transient transfection into primary cultures of chicken embryo cardiac and skeletal muscle cells, and fibroblast cultures. This approach has been used successfully in characterization of muscle actin gene promoters, see Bergsma, D. J., et al., *Mol. Cell Biol.* 6, 2462 (1986); Grichnick, J. M., et al., *Nucl. Acids Res.* 14, 1683 (1986); and Miwa, T. and Kedes, L., *Proc. Natl. Acad. Sci. U.S.A.* 83, 7653 (1986). However, no direct comparison has been made of the activity of one muscle promoter in both cardiac and skeletal muscle cells. We found that direct comparisons of transcriptional activity of cTNT-CAT constructions in cardiac and skeletal muscle cells were complicated by the fact that transfected DNA enters each cell type with very different efficiencies. While approximately 2% of skeletal muscle cells were CAT-positive by immunofluorescence, the percentage of CAT-positive myocardial cells was an order of magnitude lower (compare Tables 4 and 5). To calibrate the strength of each cTNT promoter/upstream segment in each cell type, therefore, we have compared the level of CAT activity under their control to that directed by the promoters of the chicken beta-actin gene and the Rous sarcoma virus LTR, which are strong cellular and viral promoters, respectively. In our hands, neither of these standard promoters showed any appreciable degree of cell specificity, as evidenced by the fact that they are highly active in all cell types tested and that their activity relative to each other remained relatively constant in the cell types tested (Tables 1 and 3). The most active cTNT upstream segment in both cardiac and skeletal muscle cells (cTNT-550) directed levels of CAT activity equivalent to that directed by the beta-actin promoter, indicating that the cTNT promoter is a relatively strong promoter in cardiac and skeletal muscle cells. Moreover, the similarity in maximal activity of cTNT-550 in both cardiac and skeletal muscle cells served as a means for comparing the effects of other deletions in the two cell types. FIGS. 5 summarizes the data from Table 1 by comparing the relative activity of each upstream region of the cTNT gene in the two cell types. Our results show that while different minimum promoter/upstream regions are required for efficient activity in each cell type, other non-essential upstream regions may act in a similar manner in both cell types to modify the activity of those minimum regions.

A. THE MINIMUM REGIONS REQUIRED FOR EXPRESSION OF THE cTNT PROMOTER IN CARDIAC AND SKELETAL MUSCLE CELLS

Embryonic cardiac and skeletal muscles differ in the minimum 5' flanking regions required for cTNT gene expression. The minimum active segment in cardiac cells contains 268 upstream nucleotides (FIG. 5b). The activity of the −268 segment is approximately one-third that of the most active segment which contains 550 upstream nucleotides (see FIG. 5a, and below). Deletion of 67 nucleotides, to position −201, abolishes activity (FIG. 5a and Table 1), to a level comparable to pBR-CAT which lacks a eucaryotic promoter, see Walker, M. D. et al., *Nature* 300, 557 (1983). This indicates that, as a minimum, the 67 nucleotide segment between positions −268 and −201 contains DNA sequences which are required for efficient expression of the cTNT promoter in embryonic cardiac cells. Obviously, sequences downstream of the −201 position may also be required (for example, see cTNT-268[delta−49/+38], Table 1), but these are not sufficient for expression in cardiac cells in the absence of the −268 to −201 segment.

Figure 5A:
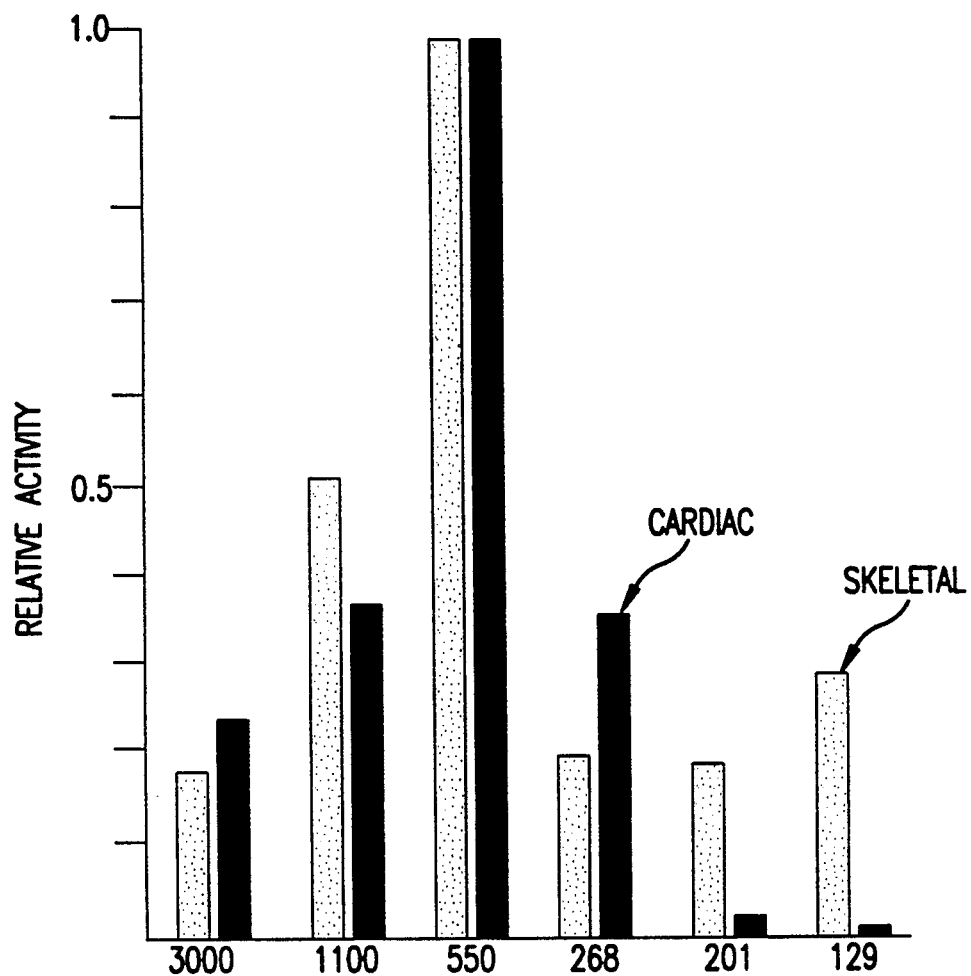
Figure 5B:
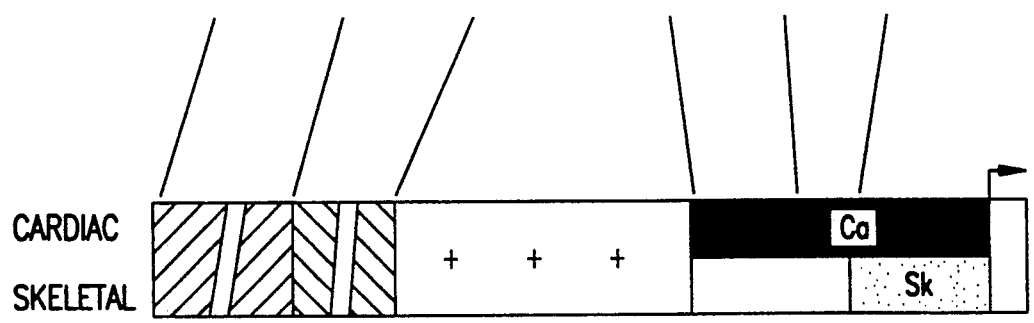

In embryonic skeletal muscle cells, on the other hand, a segment containing only 129 nucleotides upstream of the transcription initiation site is sufficient to direct approximately one-third of maximal expression (FIGS. 5a, b). Deletion to position −49 abolishes activity, reducing it to a level comparable to that of pBR-CAT (Table 1). This indicates that sequences within the segment between positions −129 and −49 are required for efficient expression in skeletal muscle cells. Addition of the segment required for efficient cardiac expression (up to −268) has a neutral, or slightly negative, effect upon cTNT promoter expression in embryonic skeletal muscle cells. We conclude, therefore, that the minimum required segments for efficient expression of the cTNT promoter in embryonic cardiac and skeletal muscle cells are different.

B. NONESSENTIAL UPSTREAM REGIONS HAVE SIMILAR EFFECTS IN BOTH CARDIAC AND SKELETAL MUSCLE CELLS

Our deletion experiments also indicate that inclusion of two upstream regions can affect the activity of the minimum cTNT promoter segments in the two cell types. While neither region is required for the activity of the minimum segments, the effect of each region is similar in both cell types. One of these, residing between positions −550 and −269, increases the level of expression of the minimum cTNT promoter approximately three-fold in both skeletal and cardiac muscle cells (FIG. 5). Inclusion of the upstream region between positions −3000 and −550 appears to have a negative effect on CAT expression, essentially abolishing the apparent positive effect conferred by the −550/−269 region. Negative-acting upstream sequences have been found in many genes, see Boss, J. M. and Strominger, J. L., Proc. Natl. Acad. Sci. U.S.A. 83, 9139 (1986); Gonzales, F. J. and Nebert, D. W., Nucl. Acids Res. 18, 7269 (1985); Gorman, C. M. et al., Cell 42, 519 (1985); Laimins, L. et al., Proc. Natl. Acad. Sci. U.S.A. 83, 3151 (1986); Muglia, L. and Rothman-Denes, L. B., Proc. Natl. Acad. Sci. U.S.A. 83, 7653 (1986); and Nir, U. et al., Proc. Natl. Acad. Sci. U.S.A. 83, 3180 (1986), although their role in vivo is not yet clear. The magnitude of the effects that these two upstream regions have upon CAT activity, although reproducible, is quite small which raises the possibility that these effects are artifactual interactions between cTNT upstream sequences and host vector sequences which can affect the activity of passenger promoters.

When the −550/−269 region is placed upstream of the HJSV tk promoter, in a pUC-based plasmid vector, it is also able to potentiate CAT expression approximately two- to three-fold, in a position- and orientation-independent manner (FIG. 3). The magnitude of this affect is similar to that observed for this segment in its native position within the cTNT upstream region (FIG. 5). Moreover, the potentiating effect is observed in skeletal muscle cells, but not in fibroblast cells (FIGS. 3b, c). These results are consistent with the conclusion that the −550/−269 region contains a muscle specific transcriptional enhancer. Preliminary experiments suggest a similar potentiating effect in cardiac cultures (data not shown) but are complicated in their interpretation by the preferential transfection of non-myocardial cells in these experiments. Nevertheless, the relatively modest effects of the putative enhancer (−550/−269) and negative-acting (−3000/−500) regions indicate that further work will be required to unequivocally define their roles, if any, in the regulation of the cTNT promoter in cardiac and skeletal muscle cells.

C. SEQUENCES CONTROLLING TISSUE SPECIFICITY OF THE cTNT PROMOTER

Transfection of the cTNT-CAT genes into embryonic cardiac and skeletal muscle cells demonstrated that the activities of minimal active promoter segments are about two-orders of magnitude higher than in fibroblast cells (Table 3). Therefore, a high degree of cell specificity resides within the minimum promoter segments defined by these experiments. However, when the upstream DNA is extended to position −550 (cTNT-550) expression in cardiac and skeletal muscle cells is over 400- and 700-fold higher than in fibroblast cells. Thus, the presence of the −550/−269 segment has a modest quantitative effect upon the level of expression, as well as a modest qualitative effect upon the degree of cell specificity. As noted above, such modest affects from upstream segments can be difficult to discern from spacing affects. Nevertheless, in experiments with heterologous promoters, the potentiating effect of the −550/−269 segment appears to be cell specific. Thus, the overall cell specificity of the cTNT promoter may result from a combination of effects from separate domains. Such combinatorial activity of upstream elements has been shown to be important for cell specific expression of the vertebrate insulin, chymotrypsin, see Edlund, T. et al., Science 230, 912 (1985) and Walkers M. D. et al., Nature 300, 557 (1983), and immunoglobulin, see Grosschedl, R. and Baltimore, D., Cell 41, 855 (1985) and Mason, J. O. et al., Cell 41, 479 (1985) ,genes. Moreover, the multiple cell specificities of the mouse aloha fetoprotein gene are determined by the combinatorial interaction of multiple upstream enhancers, each carrying a different cell tropism. See Godbout, R. et al., Mol. Cell Biol. 6, 477 (1986); and Hamer, R. E. et al, Science 235, 53 (1987). In Drosophila, the tissue and/or stage specific expression of the white, see Levis, R. et al., EMBO J. 4, 3501 (1985); Pirrotta, H. et al., EMBO J. 4, 3501 (1985), hsp26, see Dohen, R. S. and Meselson, M., Cell 43, 737 (1985), fushi tarazu, see Hiromi, Y. and Kuroiwa, A., Cell 43, 603 (1985), and yolk protein genes, see Garabedian, M. J. et al., Proc. Natl. Acad. Sci. U.S.A. 82, 1396 (1985), has also been shown to be controlled by multiple upstream sequences. The cTNT gene differs from the above examples in that the contribution of upstream regions is neither strong nor required for cell specific function of the cTNT minimum promoter segments defined here. We conclude, therefore, that the cell specificity of the cTNT promoter is predominantly attributable to cis elements contained within its minimal promoter regions (FIG. 5b), and that elements residing farther upstream play a possibly significant, but secondary role.

The foregoing "Experimental" section is illustrative of the concept which is the present invention, and is not to be taken as limiting thereof. The invention is defined by the following claims, with equivalents of the claims to be included therein.

That which is claimed is:

1. A modified chicken troponin T gene promoter which is selectively active in skeletal muscle cells, said modified promoter consisting essentially of:
   a chicken troponin T gene essential proximal promoter element which is located between nucleotide −49 and nucleotide +1 of the chicken troponin T gene upstream region, said essential proximal promoter element being necessary for the initiation of transcription of a structural gene to be operably linked thereto, and
   a chicken troponin T gene skeletal muscle-specific regulatory element which is located between nucleotide −129 and nucleotide −49 of the chicken troponin T gene upstream region, said skeletal muscle-specific regulatory element being positioned upstream of said essential proximal promoter element and necessary for the expression of said structural gene in skeletal muscle cells.

2. A recombinant gene transfer vector comprising a structural gene operably linked to the modified chicken troponin T gene promoter of claim 1.

3. A recombinant gene transfer vector as claimed in claim 2, wherein said vector is a plasmid.

4. A recombinant gene transfer vector as claimed in claim 2, wherein said vector is a virus.

5. A recombinant gene transfer vector as claimed in claim 2, wherein said vector is a retrovirus.

6. An eukaryotic host cell transfected with the vector of claim 2, wherein said modified promoter is operable in said host cell and said structural gene includes a region coding for a ribosomal binding site operable in said host cell.

7. An eukaryotic host cell as claimed in claim 6, wherein said vector is a plasmid.

8. An eukaryotic host cell as claimed in claim 6, wherein said vector is a virus.

9. An eukaryotic host cell as claimed in claim 6, wherein said vector is a retrovirus.

10. An eukaryotic host cell as claimed in claim 6, wherein said host cell is an avian cell.

11. An eukaryotic host cell as claimed in claim 6, wherein said host cell is a mammalian cell.

* * * * *

UNITED STATES PATENT AND TRADEMARK OFFICE
CERTIFICATE OF CORRECTION

PATENT NO. : 5,266,488
DATED : November 30, 1993
INVENTOR(S) : Charles P. Ordahl, et. al.

It is certified that error appears in the above-indentified patent and that said Letters Patent is hereby corrected as shown below:

Column 1, Line 58, correct "con he" to read --containing the--.

Column 2, Line 27, after first add --38--.

Column 3, Line 3, correct "sits" to read --site--.

Column 4, Line 50, correct "oft" to read --of--.

Column 7, Line 7, take out " # ".

Column 7, Line 25, correct "59," to read --99,--.

Column 7, Line 57, correct "Rubin, 9" to read --Rubin, H--.

Column 7, Line 56, correct "elating" to read --plating--.

Column 10, Line 54, take out " # ".

Column 12, Line 52, correct "promoter/" to read --promoter,--.

Signed and Sealed this

Twenty-eighth Day of June, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,266,488
DATED : November 30, 1993
INVENTOR(S) : Charles P. Ordahl, et al.

It is certified that error appears in the above-indentified patent and that said Letters Patent is hereby corrected as shown below:

Column 1, line 7, insert --This invention was made with govenrment support under Grant No. GM 32018 and HL 35561 awarded by the Department of Health and Human Services. The govenment has certain rights in the invention. --

Signed and Sealed this

Twenty-ninth Day of August, 1995

Attest:

BRUCE LEHMAN

Attesting Officer

Commissioner of Patents and Trademarks